(12) United States Patent
Childers et al.

(10) Patent No.: US 7,781,724 B2
(45) Date of Patent: Aug. 24, 2010

(54) FIBER OPTIC POSITION AND SHAPE SENSING DEVICE AND METHOD RELATING THERETO

(75) Inventors: Brooks A. Childers, Christiansburg, VA (US); Dawn K. Gifford, Blacksburg, VA (US); Roger G. Duncan, Christiansburg, VA (US); Matthew T. Raum, Chesapeake, VA (US); Michael E. Vercellino, Gretna, VA (US); Mark E. Froggatt, Blacksburg, VA (US)

(73) Assignee: Luna Innovations Incorporated, Roanoke, VA (US)

( * ) Notice: Subject to any disclaimer, the term of this patent is extended or adjusted under 35 U.S.C. 154(b) by 0 days.

(21) Appl. No.: 11/535,438

(22) Filed: Sep. 26, 2006

(65) Prior Publication Data

US 2007/0065077 A1    Mar. 22, 2007

Related U.S. Application Data

(63) Continuation-in-part of application No. 11/180,389, filed on Jul. 13, 2005, now abandoned.

(60) Provisional application No. 60/588,336, filed on Jul. 16, 2004.

(51) Int. Cl.
*G01J 1/04* (2006.01)

(52) U.S. Cl. ............................ 250/227.14; 250/227.23

(58) Field of Classification Search ............ 250/227.14, 250/227.11, 227.23, 227.18, 227.21; 356/73.1; 385/12, 13, 123, 126, 124
See application file for complete search history.

(56) References Cited

U.S. PATENT DOCUMENTS 4,295,738 A    10/1981    Meltz et al.

(Continued)

FOREIGN PATENT DOCUMENTS

WO    WO 2007/109778    9/2007

(Continued)

OTHER PUBLICATIONS

Alan D. Kersey et al., Fiber Grating Sensors, Journal of Lightwave Technology, Aug. 1997, p. 1442-1463, vol. 15, No. 8.

(Continued)

*Primary Examiner*—Que T Le
*Assistant Examiner*—Pascal M Bui-Pho
(74) *Attorney, Agent, or Firm*—Nixon & Vanderhye P.C.

(57) ABSTRACT

The present invention is directed toward a fiber optic position and shape sensing device and the method of use. The device comprises an optical fiber means. The optical fiber means comprises either at least two single core optical fibers or a multicore optical fiber having at least two fiber cores. In either case, the fiber cores are spaced apart such that mode coupling between the fiber cores is minimized. An array of fiber Bragg gratings are disposed within each fiber core and a frequency domain reflectometer is positioned in an operable relationship to the optical fiber means. In use, the device is affixed to an object. Strain on the optical fiber is measured and the strain measurements correlated to local bend measurements. Local bend measurements are integrated to determine position and/or shape of the object.

47 Claims, 11 Drawing Sheets

U.S. PATENT DOCUMENTS

| | | | |
|---|---|---|---|
| 4,443,698 A | | 4/1984 | Schiffner |
| 4,761,073 A | | 8/1988 | Meltz et al. |
| 4,996,419 A | | 2/1991 | Morey |
| 5,144,690 A | | 9/1992 | Domash |
| 5,317,147 A | | 5/1994 | Dandliker et al. |
| 5,426,297 A | | 6/1995 | Dunphy et al. |
| 5,563,967 A | * | 10/1996 | Haake ......................... 385/12 |
| 5,798,521 A | * | 8/1998 | Froggatt ................ 250/227.19 |
| 5,930,435 A | * | 7/1999 | Laming et al. ............. 385/126 |
| 6,097,488 A | | 8/2000 | Grek et al. |
| 6,154,594 A | | 11/2000 | Fiacco et al. |
| 6,160,943 A | | 12/2000 | Davis et al. |
| 6,229,599 B1 | | 5/2001 | Galtarossa |
| 6,256,090 B1 | * | 7/2001 | Chen et al. ................. 356/73.1 |
| 6,301,420 B1 | | 10/2001 | Greenaway et al. |
| 6,389,187 B1 | | 5/2002 | Greenaway et al. |
| 6,426,496 B1 | | 7/2002 | Froggatt et al. |
| 6,470,205 B2 | | 10/2002 | Bosselmann et al. |
| 6,471,710 B1 | | 10/2002 | Bucholtz |
| 6,545,760 B1 | | 4/2003 | Froggatt et al. |
| 6,636,041 B2 | | 10/2003 | Arz et al. |
| 6,668,105 B2 | | 12/2003 | Chen et al. |
| 6,878,926 B2 | | 4/2005 | Martinez et al. |
| 6,888,623 B2 | | 5/2005 | Clements |
| 6,946,646 B2 | | 9/2005 | Chen et al. |
| 7,003,184 B2 | | 2/2006 | Ronnekleiv et al. |
| 7,126,678 B2 | | 10/2006 | Fayolle et al. |
| 7,245,791 B2 | * | 7/2007 | Rambow et al. ............. 385/12 |
| 7,324,714 B1 | | 1/2008 | Cranch et al. |
| 7,330,245 B2 | | 2/2008 | Froggatt |
| 7,424,193 B2 | | 9/2008 | Galvanauskas |
| 7,440,087 B2 | | 10/2008 | Froggatt et al. |
| 2001/0021843 A1 | * | 9/2001 | Bosselmann et al. ........... 606/2 |
| 2002/0159134 A1 | | 10/2002 | Ghera et al. |
| 2004/0067003 A1 | * | 4/2004 | Chliaguine et al. ........... 385/13 |
| 2006/0013523 A1 | | 1/2006 | Childers et al. |
| 2007/0012872 A1 | | 1/2007 | Poland et al. |
| 2007/0032723 A1 | | 2/2007 | Glossop |
| 2007/0060847 A1 | | 3/2007 | Leo et al. |
| 2007/0151391 A1 | | 7/2007 | Larkin et al. |
| 2007/0156019 A1 | | 7/2007 | Larkin et al. |
| 2007/0201793 A1 | | 8/2007 | Askins et al. |
| 2007/0265503 A1 | | 11/2007 | Schlesinger et al. |
| 2008/0212082 A1 | | 9/2008 | Froggatt |
| 2008/0218770 A1 | | 9/2008 | Moll et al. |
| 2008/0285909 A1 | * | 11/2008 | Younge et al. ................ 385/13 |
| 2009/0123111 A1 | | 5/2009 | Udd |

FOREIGN PATENT DOCUMENTS

| | | |
|---|---|---|
| WO | WO2007/109778 A1 | 9/2007 |
| WO | WO 2008/131303 | 10/2008 |
| WO | WO 2009/064629 | 5/2009 |

OTHER PUBLICATIONS

Mark Froggatt et al., Distributed Measurement of Static Strain in an Optical Fiber with Multiple Bragg Gratings at Nominally Equal Wavelengths, Applied Optics, Apr. 1, 1998.

Mark Froggatt, Distributed Measurement of the Complex Modulation of a Photoinduced Bragg Grating in an Optical Fiber, Applied Optics, Sep. 1, 1996.

P.M. Blanchard et al., Two-Dimensional Bend Sensing with a Single, Multi-Core Optical Fiber, Smart Mater. Struct., 2000, p. 132-140, vol. 9.

Roger Duncan, Sensing Shape, SPIE's OEMagazine, Sep. 2005, p. 18-21, vol. 5, No. 8, SPIE, US.

David Q. Larkin et al., "Modular Decoupled Force Sensor," U.S. Appl. No. 60/755,157, filed Dec. 30, 2005.

Alan D. Kersey et al., Fiber Grating Sensors, Journal of Llghtwave Technology, Aug. 1997, p. 1442-1463, vol. 15, No. 8.

Mark Froggatt et al., Distributed Measurement of Static Strain in an Optical Fiber with Multiple Bragg Gratings at Nominally Equal Wavelengths, Applied Optics, Apr. 1, 1998, p. 1741-1746, vol. 37, No. 10.

Mark Froggatt, Distributed Measurement of the Complex Modulation of a Photoinduced Bragg Grating in an Optical Fiber, Applied Optics, Sep. 1, 1996, p. 5162-5164, vol. 35, No. 25.

Mark Wippich and Kathy Li Dessau, "Tunable Lasers and Fiber-Bragg-Grating Sensors", The Industrial Physicist, Jun./Jul. 2003, pp. 24-27, American Institute of Physics.

G.M.H. Flockhart, et al., "Two-axis bend measurement with Bragg gratings in multicore optical fiber," Optics Letters, Mar. 15, 2003, pp. 387-389, vol. 28, No. 6, Optical Society of America.

Gary A. Miller, et al., "Shape sensing using distributed fiber optic strain measurements," Proceedings of SPIE, 2004, pp. 528-531, vol. 5502, SPIE.

M.A. Davis, et al., "Fiber Optic Bragg Grating Array for Shape and Vibration Mode Sensing," SPIE, pp. 94-102, vol. 2191.

Sandra M. Klute, et al., "Fiber-Optic Shape Sensing and Distributed Strain Measurements on a Morphing Chevron," American Institute of Aeronautics and Astronautics, 2006, pp. 1-23.

Roger G. Duncan and Matthew T. Raum, "Fiber-Optic Shape and Position Sensing," Proceedings of the 5th International Conference on Structural Health Monitoring, 2005.

Joseph R. Blandino et al., "Three-Dimensional Shape Sensing for Inflatable Booms,"Proceedings of the 46th AIAA/ASME/ASCE/Ahs/ASC Structures, Structural Dynamics and Materials Conference, 2005.

Roger G. Duncan and Matthew T. Raum, "Characterization of a Fiber-Optic Shape and Position Sensor," SPIE International Symposium on Smart Structures and Materials, Proc. SPIE 6167-4, 2006.

U.S. Appl. No. 11/180,389, filed Jul. 13, 2005, Childers.

U.S. Appl. No. 11/062,740, filed Feb. 23, 2005, Inventor: Froggatt.

U.S. Appl. No. 11/371,229, filed Mar. 9, 2006; Inventor: Froggatt.

U.S. Appl. No. 11/808,260, filed Jun. 7, 2007; Inventor: Froggatt.

U.S. Appl. No. 12/047,056, filed Mar. 12, 2008; Inventor: Froggatt.

International Search Report and Written Opinion mailed Jun. 24, 2008 in corresponding PCT Application PCT/US08/03236.

Huttner et al., "Local Birefringence Measurements in Single-Mode Fibers with Coherent Optical Frequency-Domain Reflectometer", IEEE Photonics Technology Letters, vol. 10, No. 10, Oct. 1998.

Limberger et al., "OLCR Characterization of Efficient Bragg Gratings in Optical Fiber", SPIE vol. 2044, Aug. 17, 1993, pp. 272-283.

Wayne V. Sorin, "High Resolution Optical Fiber Reflectometry Techniques", SPIE vol. 1797 Distributed and Multiplexed Fiber Optic Sensors II (1992); pp. 109-118.

Duncan, R. et al., "Characterization of a Fiber-Optic Shape and Position Sensor," SPIE International Symposium on Smart Structures and Materials, Proc. SPIE 6167-4 (2006).

Duncan, R. et al., "Fiber-Optic Shape and Position Sensing," Proceedings of the $5^{th}$ International Conference on Structural Health Monitoring (2005).

Duncan, R. et al., "Use of a Fiber-Optic Distributed Sensing System for Nondestructive Testing of Aerospace Structures," Materials Evaluation 61, 838 (2003).

Duncan, R. et al., "A Distributed Sensing Technique for Aerospace Applications," $42^{nd}$ AIAA Aerospace Sciences Meeting (2004), pp. 1-8.

Duncan, R. et al., "High-Accuracy Fiber-Optic Shape Sensing," SPIE International Symposium on Smart Structures and Materials, Proc. SPIE 6530-650 (2007).

Duncan, R., Sensing Shape, SPIE's OEMagazine, Sep. 2005, pp. 18-21, vol. 5, No. 8, SPIE, US.

Froggatt, M. et al., "Correlation and Keying of Rayleigh Scatter for Loss and Temperature Sensing in Parallel Optical Networks," OFC Technical Digest, paper PDP 17, 2004.

Froggatt, M. et al., "High Resolution Strain Measurement in Optical Fiber with Rayleigh Scatter," Appl. Opt., 37, 1735-1740, Apr. 1, 1998.

Froggatt et al., "Distributed Strain and Temperature Discrimination in Unaltered Polarization Maintaining Fiber," Optical Fiber Sensors, OSA Technical Digest (CD), Optical Society of America, 2006, paper ThC5.

Eickoff, W. et al., "Optical Frequency Domain Reflectometry in single-Mode Fiber," Appl. Phys. Lett. 39 (9), 693-695, Nov. 1, 1981.

Childers, B. et al., "Recent Developments in the Application of Optical Frequency Domain Reflectometry to Distributed Bragg Grating Sensing," Fiber Optic Sensor Technology and Applications 2001, Proc. SPIE 4578 (2001), pp. 19-31.

Childers, B. et al., "Use of 3000 Bragg Grating Strain Sensors Distributed on Four Eight-Meter Optical Fibers During Static Load Tests of a Composite Structure," Smart Structures and Materials Conference, Proc. SPIE vol. 4332 (2001), pp. 133-142.

Kreger, S. et al., "High Resolution Distributed Strain or Temperature Measurements in Single- and Multi-mode Fiber Using Swept-Wavelength Interferometry," OFS 18 Technical Digest, Cancun, Mexico, Oct. 2006, paper ThE42.

Kreger, S. et al., "Return Loss Measurement in the Presence of Variable Insertion Loss Using Optical Frequency Domain Reflectometry", NIST Symposium for Photonic and Fiber Measurements, Sep. 19, 2006.

Sang et al., "High-Resolution Extended Distance Distributed Strain Measurements Using Swept-Wavelength Interferometry", Proceedings of EPRI's $3^{rd}$ Increased Power Flow Conference (Aug. 2006).

Sorin, High Resolution Optical Fiber Reflectometry Techniques, SPIE vol. 1797 Distributed and Multiplexed Fiber Optic Sensors II (1992), pp. 109-118.

U.S. Appl. No. 11/690,116, filed Mar. 22, 2007; Inventor: Schlesinger et al.

U.S. Appl. No. 12/106,254, filed Apr. 18, 2008; Inventor: Younge et al.

U.S. Appl. No, 12/236,478, filed Sep. 23, 2008; Inventor: Udd.

* cited by examiner

FIBER OPTIC POSITION AND SHAPE SENSING DEVICE AND METHOD RELATING THERETO

CROSS-REFERENCE TO RELATED APPLICATIONS

This application is a continuation-in-part of U.S. patent application Ser. No. 11/180,389, entitled, "Fiber Optic Position and Shape Sensing Device and Method Relating Thereto," filed Jul. 13, 2005, now abandoned, which claims the benefit of U.S. Provisional Patent Application No. 60/588,336, entitled, "Fiber-Optic Shape and Relative Position Sensing," filed Jul. 16, 2004, both of which are hereby incorporated by reference in their entirety.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract Nos. NNL04AB25P and NNG04CA59C awarded by the National Aeronautics and Space Administration.

FIELD OF THE INVENTION

The present invention relates to fiber optic sensing. In particular, it relates to fiber optic sensors that are capable of determining position and shape of an object.

BACKGROUND OF THE INVENTION

Fiber optic strain sensors are well established for applications in smart structures and health monitoring. The advantages of these sensors include their small size, low cost, multiplexing capabilities, immunity to electromagnetic interference, intrinsic safety and their capability to be embedded into structures.

Many structural devices and objects undergo various shape changes when exposed to certain environments. In some instances, it is necessary to know the degree of change and to compensate for these changes. By embedding or attaching a sensor to the structure, one is able to monitor the dynamic shape or relative position of the structure independently from temperature or load effects. Further by measuring the dynamic shape of a structure, the state of flexible structures can be established. When a degradation occurs, it can be corrected using signal processing.

Some have tried to measure shape changes by using foil strain gauges. These sensors, while sufficient for making local bend measurements, are impractical for use with sufficient spatial resolution to reconstruct shape or relative position over all but the smallest of distances. Others have used fiber optic micro-bend sensors to measure shape. This approach relies on losses in the optical fiber which cannot be controlled in a real-world application.

Clements (U.S. Pat. No. 6,888,623 B2) describes a fiber optic sensor for precision 3-D position measurement. The central system component of the invention is a flexible "smart cable" which enables accurate measurement of local curvature and torsion along its length. These quantities are used to infer the position and attitude of one end of the cable relative to the other. Sufficiently accurate measurements of the local curvature and torsion along the cable allow reconstruction of the entire cable shape, including the relative position and orientation of the end points. The smart cable for making these measurements comprises a multicore optical fiber, with individual fiber cores constructed to operate in the single mode regime, but positioned close enough to cause cross-talk (mode coupling) between cores over the length of the fiber. This cross-talk is very sensitive to the distribution of strain (curvature and torsion) along the cable. Clements describes the errors in measured curvature as being divided into three classes: those due to instrument noise, systematic errors due to fabrication defects (core geometry, index of refraction variations, etc.) and sensitivity to extrinsic variables such as temperature. Of the three, instrument noise is probably the worst threat to successful shape inversion. Several approaches are proposed to mitigating effects of instrument noise, including time averaging and diversity measurements using fibers with redundant cores or multiple multicore fibers. A plurality of single mode cores may also be provided in an optical medium comprising a flexible sheet of material.

Greenaway et al. (U.S. Pat. No. 6,301,420 B1) describe a multicore optical fiber for transmitting radiation. The optical fiber comprises two or more core regions, each core region comprising a substantially transparent core material and having a core refractive index, a core length, and a core diameter. The core regions are arranged within a cladding region. The cladding region comprises a length of first substantially transparent cladding material having a first refractive index. The first substantially transparent cladding material has an array of lengths of a second cladding material embedded along its length. The second cladding material has a second refractive index which is less than the first refractive index, such that radiation input to the fiber propagates along at least one of the core regions. The cladding region and the core regions may be arranged such that radiation input to the optical fiber propagates along one or more of the lengths of the core regions in a single mode of propagation. The optical fiber may be used as a bend sensor, a spectral filter or a directional coupler. A bend sensor comprises a multicore photonic crystal fiber. The measurement of the relative shift in the fringe pattern provides an indication of the extent by which the fiber is bent. If the fiber is embedded in a structure, an indication of the extent to which the structure is bent is provided. This type of system is an intensity based system, in contrast to an internal reflection system, therefore light is not guided by an internal reflection mode and, hence, the system is not as accurate as an internal reflection system.

Greenway et al. (U.S. Pat. No. 6,389,187 B1) describe an optical fiber bend sensor that measures the degree and orientation of bending present in a sensor length portion of a fiber assembly. Within a multicored fiber, cores are grouped in non-coplanar pairs. An arrangement of optical elements define within each core pair two optical paths which differ along the sensor length. One core of a pair is included in the first path and the other core in the second path. A general bending of the sensor region will lengthen one core with respect to the other. Interrogation of this length differential by means of interferometry generates interferograms from which the degree of bending in the plane of the core pair is extracted. Bend orientation can be deduced from data extracted from multiple core pairs. The apparatus is capable of determining bending of the sensor length, perhaps as a consequence of strain within an embedding structure, by monitoring that component of the bend in the plane of two fiber cores within the sensor length. Interferograms are formed between radiation propagating along two different optical paths, the optical paths differing within a specific region of the fiber. This region, the sensor length, may be only a fraction of the total fiber length. Generally, bending this sensing region will inevitably lengthen one core with respect to the other. Interrogation of this length differential by means of interferometry provides an accurate tool with which to measure bending. Moreover, defining a sensor length down a potentially long fiber downlead enables strains to be detected at a localized region remote from the radiation input end of the fiber. Thus, the fiber assembly can be incorporated in, for example, a building wall, and strains developing in the deep interior of the wall measured.

The first and second cores constitute a core pair and component cores of the multicore fiber preferably comprise an arrangement of such core pairs. The coupling means may accordingly be arranged to couple and reflect a portion of radiation propagating in the first core into the second core of the respective pair. This provides the advantage of flexibility. The optical path difference arising between any core pair can be interrogated, enabling the selection of planes any of which may be the plane in which components of a general bend curvature may be measured.

Schiffner (U.S. Pat. No. 4,443,698) describes a sensing device having a multicore optical fiber as a sensing element. The sensing device includes a sensing element in the form of an optical fiber, a device for coupling light into the fiber and a device for measuring changes in the specific physical parameters of the light passing through the fiber to determine special physical influences applied to the fiber. The fiber is a multicore fiber having at least two adjacently extending cores surrounded by a common cladding and a means for measuring the alterations in the light passing through each of the cores. To make the device sensitive to bending and deformation in all directions, the fiber may have two cores and be twisted through 90 degrees or the fiber may have three or more cores which are not disposed in the same plane. The measuring of the amount of change may be by measuring the interference pattern from the superimposed beams of the output from the two cores or by measuring the intensity of each of the output beams separately. When there is no appreciable cross-coupling between the cores, an interferometric means for measurement will include a light receiving surface which is arranged in the path of light which passes through the two cores and has been brought into interference by means of superimposition. The sensing means may use a light receiving surface which is a collecting screen in which the interference pattern can be directly observed or the light receiving surface may be the light sensitive surface of a light sensitive detector which will monitor the light intensity of the interference pattern. To superimpose the light beams emitted from each of the cores, a beam divider device or devices may be utilized.

Haake (U.S. Pat. No. 5,563,967) describes a fiber optic sensor and associated sensing method including a multicore optical fiber having first and second optical cores adapted to transmit optical signals having first and second predetermined wavelengths, respectively, in a single spatial mode. The first and second optical cores each include respective Bragg gratings adapted to reflect optical signals having first and second predetermined wavelengths, respectively. Based upon the differences between the respective wavelengths of the optical signals reflected by the respective Bragg gratings and the first and second predetermined wavelengths, a predetermined physical phenomena to which the workpiece is subjected can be determined, independent of perturbations caused by other physical phenomena.

Froggatt and Moore, "Distributed Measurement of Static Strain in an Optical fiber with Multiple Bragg Gratings at Nominally Equal Wavelengths," Applied Optics, Vol. 27, No. 10, Apr. 1, 1998 describe a demodulation system to measure static strain in an optical fiber using multiple, weak, fiber Bragg gratings in a single fiber. Kersey et al. in "Fiber Grating Sensors," Journal of Lightwave Technology, Vol. 15, No. 8, Aug. 1997 describe that a primary advantage of using FBG's for distributed sensing is that large numbers of sensors may be interrogated along a single fiber. With mixed WDM (wavelength division multiplexing)/TDM (time division multiplexing) in the serial configuration several wavelength-stepped arrays are concatenated, each at a greater distance along the fiber. Two deleterious effects can arise with strong reflectors. FBG's whose reflected light signals are separated in time, but which overlap in wavelength can experience cross-talk through "multiple-reflection" and "spectral-shadowing". The WDM/TDM parallel and branching optical fiber network topologies eliminate these deleterious effects, but at the price of reduced overall optical efficiency and the need for additional couplers and stronger FBG's.

Froggatt (U.S. Pat. No. 5,798,521) describes an apparatus and method for measuring strain in Bragg gratings. Optical radiation is transmitted over a plurality of contiguous predetermined wavelength ranges into a reference optical fiber network and an optical fiber network under test to produce a plurality of reference interference fringes and measurement interference fringes, respectively. The reference and measurement fringes are detected and sampled such that each sampled value of the reference and measurement fringes is associated with a corresponding sample number. The wavelength change of the reference optical fiber, for each sample number, due to the wavelength of the optical radiation is determined. Each determined wavelength change is matched with a corresponding sampled value of each measurement fringe. Each sampled measurement fringe of each wavelength sweep is transformed into a spatial domain waveform. The spatial domain waveforms are summed to form a summation spatial domain waveform that is used to determine location of each grating with respect to a reference reflector. A portion of each spatial domain waveform that corresponds to a particular grating is determined and transformed into a corresponding frequency spectrum representation. The strain on the grating at each wavelength of optical radiation is determined by determining the difference between the current wavelength and an earlier, zero-strain wavelength measurement.

Froggatt fails to disclose the use of a frequency domain reflectometer in combination with an optical fiber means having at least two fiber cores to determine the position or shape of an object. The advantage to this arrangement is that many (hundreds to thousands) of Bragg gratings are employed, thus increasing the accuracy of the final position measurement. Rather, Froggatt's disclosure is limited to a discussion of how to determine strain based on a spatial domain waveform generated by comparing a sampled measurement fringe with a reference measurement fringe using a single core optical fiber having multiple Bragg gratings disposed therein and he specifically teaches that longer (and fewer) gratings could be used to cover the same fiber length.

Chen et al. (U.S. Pat. No. 6,256,090 B1) describe a method and apparatus for determining the shape of a flexible body. The device uses Bragg grating sensor technology and time, spatial, and wavelength division multiplexing, to produce a plurality of strain measurements along one fiber path. Using a plurality of fibers, shape determination of the body and the tow cable can be made with minimal ambiguity. The use of wavelength division multiplexing has its limitations in that the ability to have precision with respect to determining the shape and/or position of an object is limited. Wavelength division multiplexing can only be used with sensor arrays with a relatively limited number of sensors, e.g., on the order of several hundred sensors, and therefore, is insufficient for the application of determining shape and or position of an object with any precision.

An object of the present invention is to provide a fiber optic position and shape sensing device that employs an optical fiber means comprising at least two fiber cores and having an array of fiber Bragg grating's disposed therein coupled with a frequency domain reflectometer.

Another object of the present invention is to provide a method for determining position and shape of an object using the fiber optic position and shape sensing device.

SUMMARY OF THE INVENTION

By the present invention, a fiber optic position and shape sensing device is presented. In general, the device comprises an optical fiber means for determining position and shape of an object. The optical fiber means is either at least two single core optical fibers or a multicore optical fiber having at least two fiber cores. In either case, the fiber cores are spaced apart such that mode coupling between the fiber cores is minimized. An array of fiber Bragg gratings are disposed within each fiber core and a frequency domain reflectometer is positioned in an operable relationship to the optical fiber means.

In using the fiber optic position and shape sensing device of the present invention to determine the position or shape of an object, the device is affixed to an object. The strain on the optical fiber is measured and the strain measurements are correlated to local bend measurements. The local bend measurements are integrated to determine the position or shape of the object.

The device and method of the present invention are useful for providing practical shape and relative position sensing over extended lengths. The combination of high spatial resolution, achieved through the array of at least 100 fiber Bragg gratings, coupled with non-rigid attachment to the object enables higher accuracy than systems of the prior art. In particular, systems using wave division multiplexing coupled with fiber Bragg gratings are limited in range or have the inability to achieve high spatial resolution. Systems where cross-talk or mode coupling occurs between the fiber cores are difficult to implement because such arrangements are subject to measurement distortions. Lastly, the present invention does not require models of the mechanical behavior of the object in order to determine the position or shape of the object.

The fiber optic position and shape sensing device of the present invention has many uses. It is used to monitor true deflection of critical structures as well as the shape of structures. The sensing device serves as a feedback mechanism in a control system. The device is suitable for use as a monitor for the relative position of an object attached to it. For example, the device is attached to a search and rescue robot in places where GPS either possesses insufficient resolution or is unavailable. Alternatively, the device is attached to a floating buoy deployed by a ship to make differential GPS measurements. The device is also suitable for medical applications such as minimally invasive surgical techniques as well as biometric monitoring. Lastly, the device is used for performing modal analysis of mechanical structures.

Additional objects and advantages of the invention will be set forth in part in the description which follows, and in part, will be obvious from the description, or may be learned by practice of the invention. The objects and advantages of the invention will be obtained by means of instrumentalities in combinations particularly pointed out in the appended claims.

BRIEF DESCRIPTION OF THE DRAWINGS

The accompanying drawings illustrate a complete embodiment of the invention according to the best modes so far devised for the practical application of the principals thereof, and in which.

DETAILED DESCRIPTION OF THE PREFERRED EMBODIMENTS

The fiber optic position and shape sensing device of the present invention generally comprises on an optical fiber means for determining position and shape of an object. The optical fiber means comprises at least two fiber cores spaced apart from each other wherein mode coupling between the fiber cores is minimized. The device further comprises an array of fiber Bragg gratings disposed within each fiber core and a frequency domain reflectometer positioned in an operable relationship to the optical fiber means. The optical fiber means is either at least two single core optical fibers positioned in a relative relationship to one another or a multicore optical fiber having at least two fiber cores.

Figure 1A:
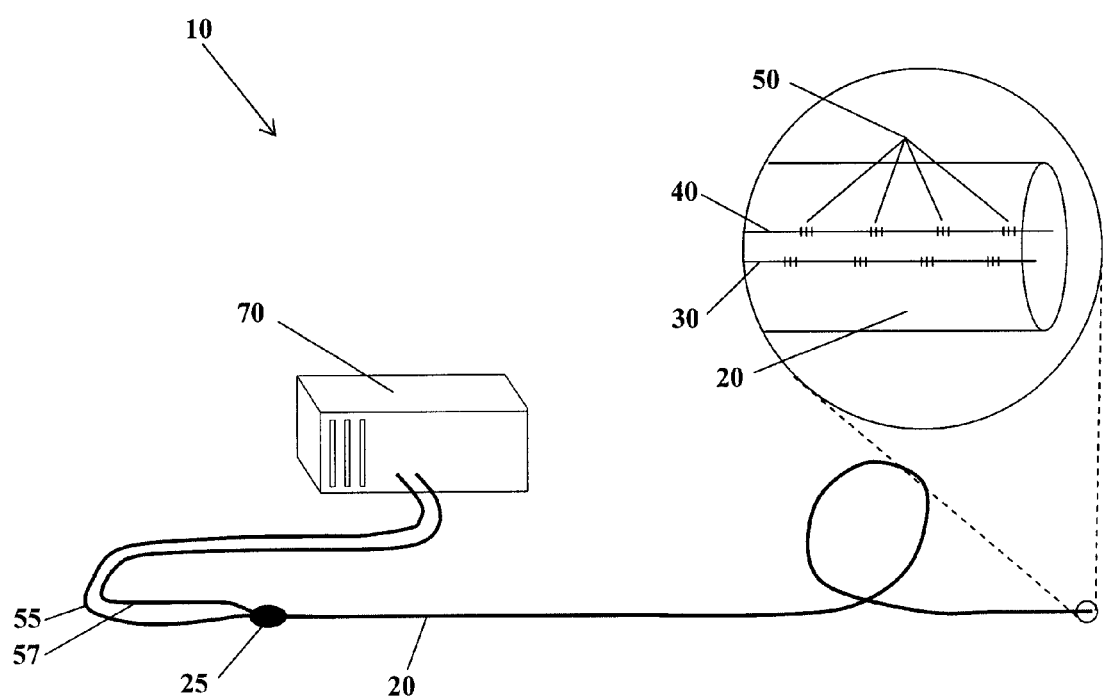
FIG. 1A is a schematic representation of a fiber optic position and shape sensing device of the present invention having two fiber cores.
Figure 1B:
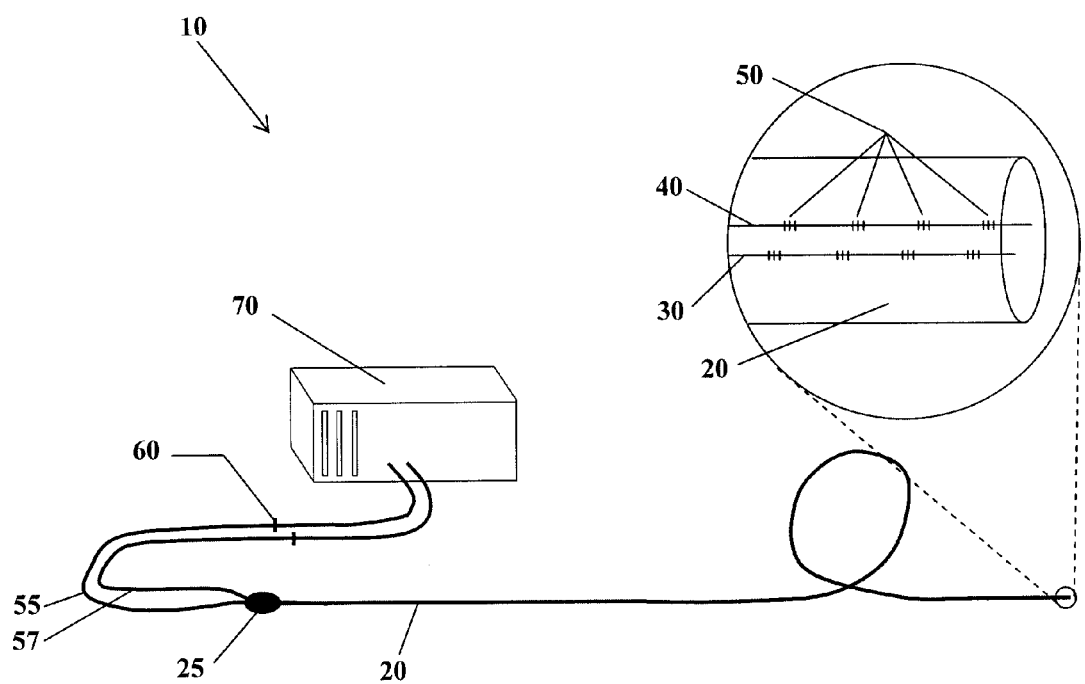
FIG. 1B is a schematic representation of a preferred embodiment of the fiber optic position and shape sensing device of the present invention having two fiber cores and a broadband reference reflector.
Figure 2A:
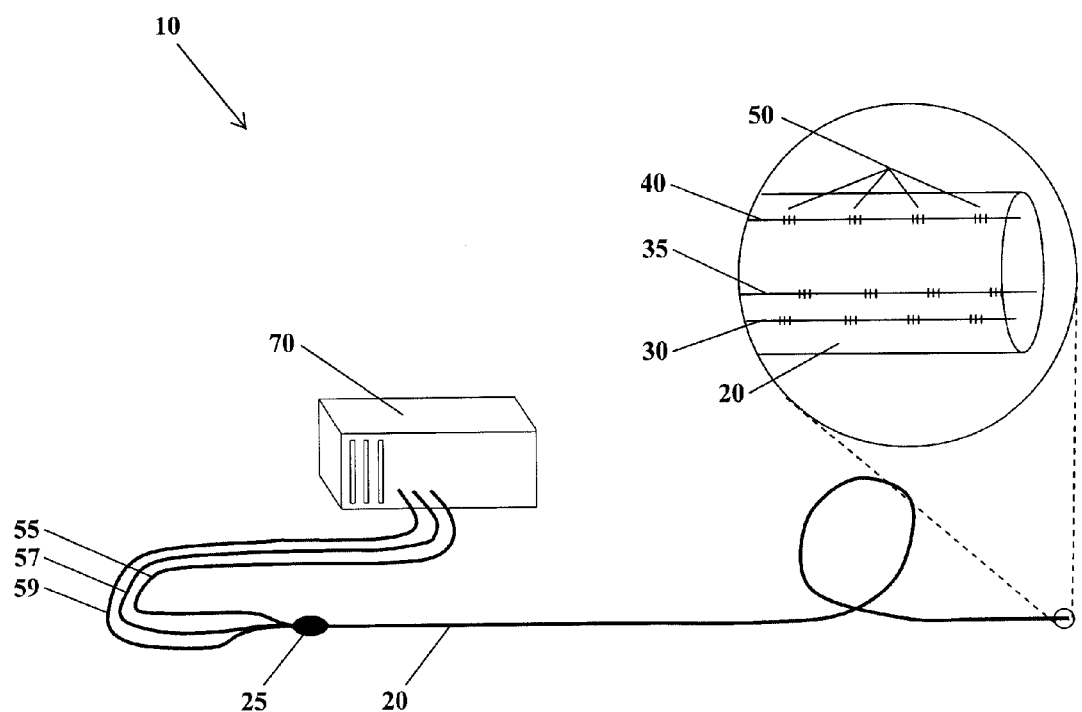
FIG. 2A is a schematic representation of a fiber optic position and shape sensing device of the present invention having three fiber cores.

Referring now to the figures where similar elements are numbered the same throughout, FIG. 1A depicts an embodiment of the fiber optic position and shape sensing device 10 of the present invention where the optical fiber means is a multicore optical fiber 20 having at least two fiber cores 30, 40 spaced apart wherein mode coupling between the fiber cores is minimized. In order to achieve optimal results, mode coupling between the fiber cores should be minimized if not completely eliminated. Applicants have found that mode coupling causes distortions. A multicore optical fiber having two fiber cores (as depicted in FIG. 1) is suitable for use as a positioning device or for determining the two dimensional shape of an object. However, when determining three dimensional shapes, the multicore optical fiber should have preferably three fiber cores 30, 35, 40 (as shown in FIG. 2A).

Multicore optical fiber is fabricated in much the same way as a standard telecommunications optical fiber. The first step in the fabrication process is to design and model the optical parameters for the preform (i.e.—refractive index profile, core/cladding diameters, etc.) to obtain the desired waveguiding performance. The fabrication of multicore optical fiber requires the modification of standard over-cladding and fiberization processes. Though numerous methods can be employed to achieve the desired geometry, the preferred methods are the multi-chuck over-cladding procedure and the stack-and-draw process. In both techniques, the original preforms with the desired dopants and numerical aperture are fabricated via the Modified Chemical Vapor Deposition (MCVD) process. The preforms are then stretched to the appropriate diameters.

Following the preform stretch, the preforms are sectioned to the appropriate lengths and inserted into a silica tube with the other glass rods to fill the voids in the tube. The variation in the two procedures arises in the method in which the preform rods are inserted into the tube. In the multi-chuck method the bait rods and preforms are positioned in the tube on a glass working lathe. A double chuck is used to align the preforms in the tube. Once positioned, the tube is collapsed on the glass rods to form the preform. The preform is then fiberized in the draw tower by a standard procedure known to those of ordinary skill in the art. In the stack-and-draw process, the preforms and the bait rods are positioned together in the silica tube, with the interstitial space filled with additional glass rods. The glass assembly is then drawn into fiber with the appropriate dimensions.

An array of fiber Bragg gratings 50 is disposed within each fiber core. Such array is defined as a plurality of fiber Bragg gratings disposed along a single fiber core. Preferably, the array comprises at least one hundred (100) fiber Bragg gratings. Each fiber Bragg grating is used to measure strain on the multicore optical fiber. Fiber Bragg gratings are fabricated by exposing photosensitive fiber to a pattern of pulsed ultraviolet light from an excimer laser, forming a periodic change in the refractive index of the core. This pattern, or grating, reflects a very narrow frequency band of light that is dependent upon the modulation period formed in the core. In its most basic operation as a sensor, a Bragg grating is either stretched or compressed by an external stimulus. This results in a change in the modulation period of the grating which, in turn, causes a shift in the frequency reflected by the grating. By measuring the shift in frequency, one can determine the magnitude of the external stimulus applied.

Figure 2B:
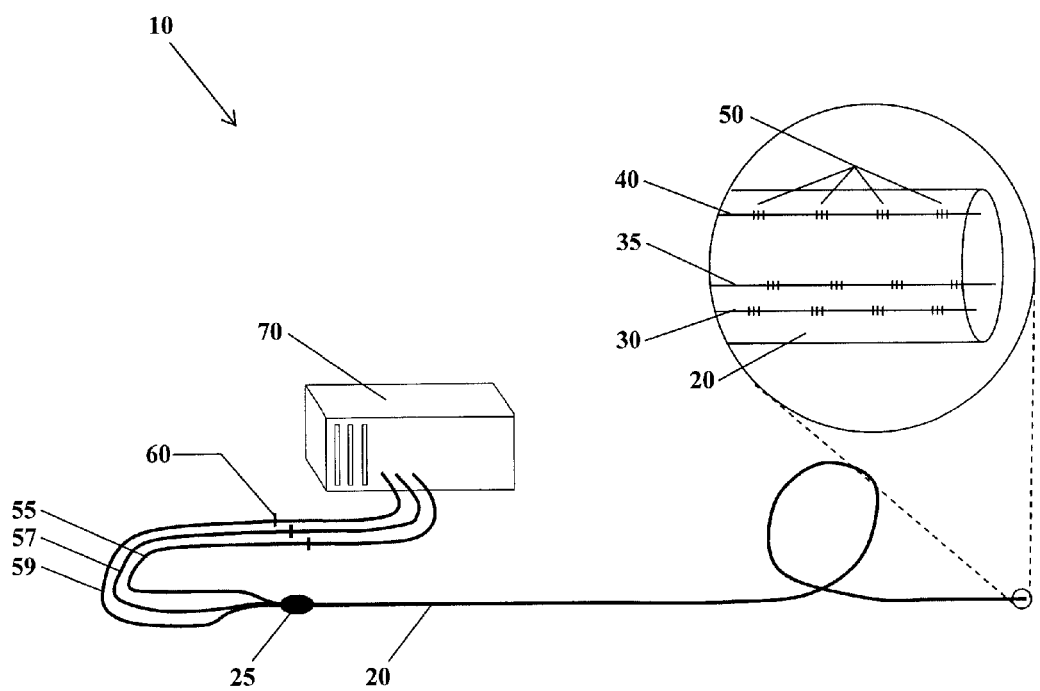
FIG. 2B is a schematic representation of a preferred embodiment of the fiber optic position and shape sensing device of the present invention having three fiber cores and a broadband reference reflector.

Referring back to FIG. 1A, the multicore optical fiber 20 is coupled to single core optical fibers 55, 57 through a coupling device 25. FIG. 2A shows an embodiment of the invention where three single core optical fibers 55, 57, 59 are coupled to the multicore optical fiber 20 through a coupling device 25. FIGS. 1B and 2B depict a preferred embodiment where each single core optical fiber 55, 57 (in FIG. 1B) or 55, 57, 59 (in FIG. 2B) has a broadband reference reflector 60 positioned in an operable relationship to each fiber Bragg grating array wherein an optical path length is established for each reflector/grating relationship. However, it is important to note that the broadband reference reflector is not necessary in order for the invention to work. Alternatively, it is well understood in the art that all optical frequency domain reflectometers include a means, such as a reflector, to establish a reference path and, therefore, a separate reflector such as the broadband reference reflector is not an essential element of the invention. Similarly, some optical frequency domain reflectometers (such as the OBR commercially available from Luna Innovations Incorporated) rely on an internal reference path, thus eliminating the need for an external broadband reference reflector altogether. As a preferred embodiment, a frequency domain reflectometer 70 is positioned in an operable relationship to the multicore optical fiber 20 through the single core optical fibers 55, 57, 59 such that the frequency domain reflectometer 70 is capable of receiving signals from the fiber Bragg gratings. As stated previously, any frequency domain reflectometer known to those of ordinary skill in the art may be employed for the present invention provided that it is capable of monitoring many Bragg gratings at one time. Preferably, the frequency domain reflectometer receives signals from the fiber Bragg grating arrays. Such a device is known as the Luna Distributed Sensing System and is commercially available from Luna Innovations Incorporated.

In further embodiments of the invention, the array of fiber Bragg gratings are co-located along the multicore optical fiber. The array preferably comprises at least one hundred (100) fiber Bragg gratings. In an alternative embodiment, a wavelength division multiplexing device is positioned in an operable relationship to the multicore optical fiber and is co-located with the frequency domain reflectometer. This arrangement allows for extension of optical fiber length if needed for a specific application, where a much smaller number (less than about one hundred (100) fiber Bragg gratings) are employed.

Figure 3:
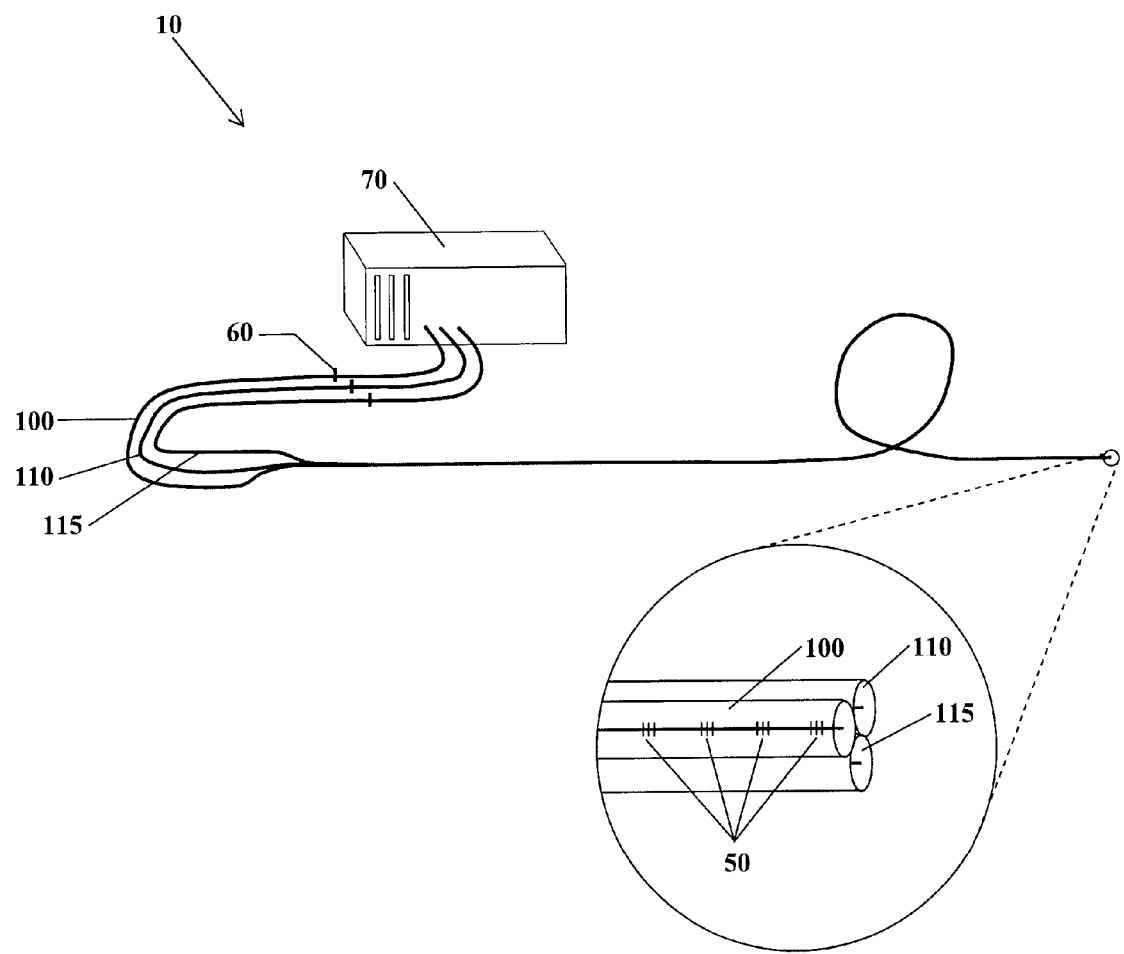
FIG. 3 depicts a preferred embodiment where the optical fiber means is three single core optical fibers.

FIG. 3 depicts an alternative preferred embodiment where the optical fiber means is at least two single core optical fibers and, preferably, is three single core optical fibers 100, 110, 115. When three single core optical fibers are used, the fiber cores are non-coplanar and form a triangular shape. Applicants have found through experimentation, preferably, that the triangular shape is such that each fiber core has a center, and each center is 120° with respect to each of the other two core centers. The 120° relationship minimizes distortions. As with the multicore optical fiber, the fiber cores are spaced apart such that mode coupling between the fiber cores is minimized. Also, as seen in the multicore optical fiber, an array of Bragg gratings 50 is disposed within each fiber core. As a preferred embodiment, a broadband reference reflector 60 is positioned in an operable relationship to each fiber Bragg grating array wherein an optical path length is established for each reflector/grating relationship, however, the broadband reference reflector 60 is not essential. A frequency domain reflectometer 70 is positioned in an operable relationship to the single core optical fibers.

Figure 4:
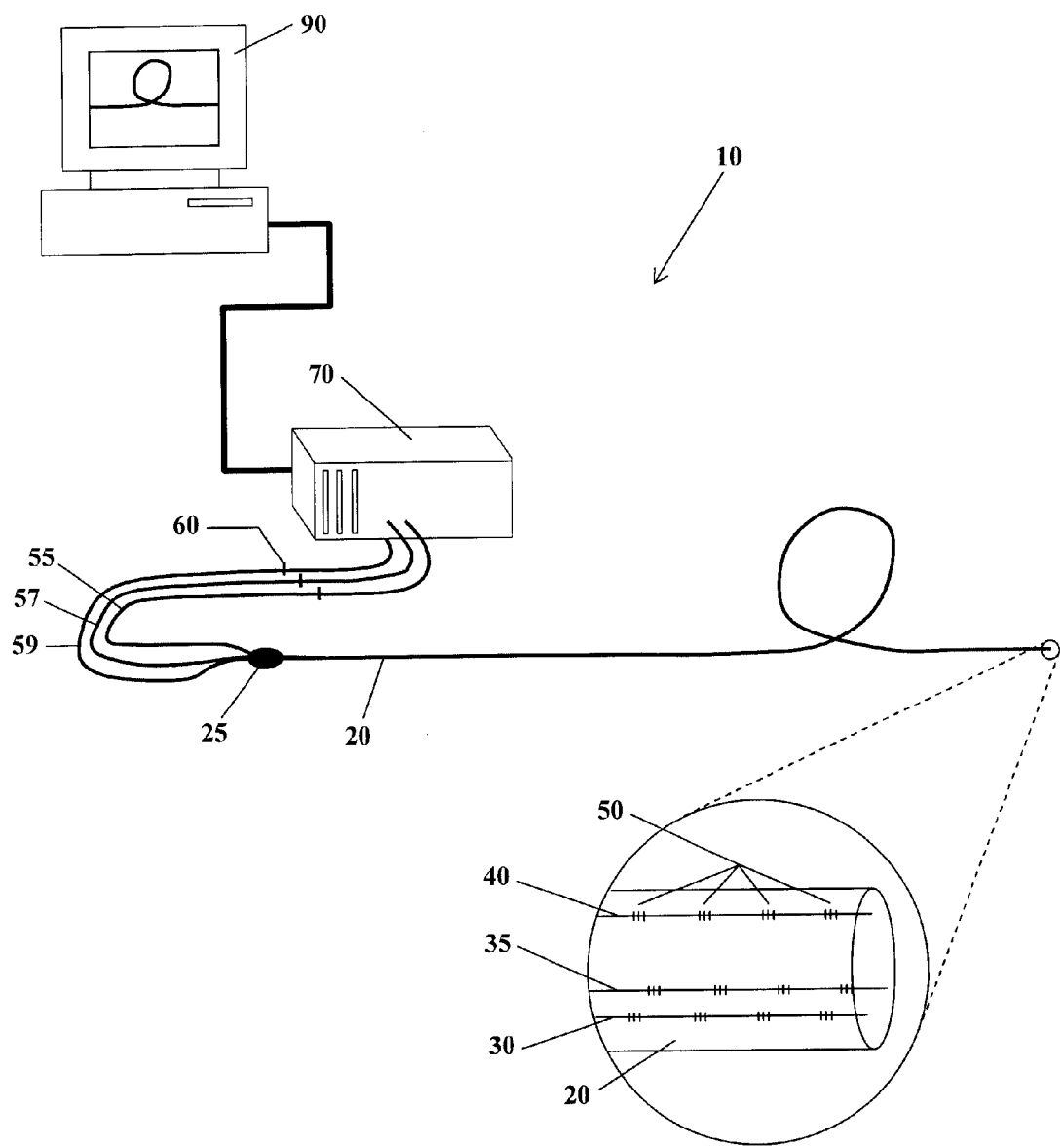
FIG. 4 is a schematic representation of an optical arrangement for the fiber optic position and shape sensing device.

In a further embodiment of the invention, shown in FIG. 4, the fiber optic position and shape sensing device 10 has a computer 90 positioned in an operable relationship to the frequency domain reflectometer 70. It is understood that the optical arrangement shown in FIG. 4 is not limited to those devices employing multicore optical fibers but that it may be used in combination with those devices employing single core optical fibers as well. The computer correlates the signals received from the frequency domain reflectometer 70 to strain measurements. These strain measurements are correlated into local bend measurements. A local bend measurement is defined as the bend between a reference sensor and the next set of sensors in the array. The local bend measurements are integrated into a position or shape. If the optical fiber means has only two cores, then shape determination is limited to two dimensions, if there are three or more cores, three dimensional shape is determined, and in both instances, position is determined.

In essence, the present invention operates on the concept of determining the shape of an object by measuring the shape of the optical fiber. Based on these measurements relative position is also ascertainable. For example, shape sensing is accomplished by creating a linear array of high spatial resolution fiber optic bend sensors. Assuming each element is sufficiently small, by knowing the curvature of the structure at each individual element the overall shape is reconstructed through an integration process. A bend sensor is created by adhering two strain sensors to either side of a flexible object or by embedding the sensors in the object. Examples of various objects include but are not limited to: a position tracking device, such as a robot, and flexible objects such as medical instruments or flexible structures. To monitor the shape of an object that can deform in three dimensions, a measure of the full vector strain is required. Hence, a minimum of three cores is required with each core containing an array of fiber Bragg grating strain sensors (preferably of at least one hundred (100) fiber Bragg gratings), preferably each sensor collocated in the axial dimension. To form an array of three dimensional bend sensors, it is assumed that, at a minimum, three optical fiber cores are fixed together such that their centers are non-coplanar. Preferably, the core centers are each 120° with respect to each of the other two core centers and form a triangular shape. It should be acknowledged that any number of optical fiber cores greater than three can also be used for three dimensional bend sensing. The separate cores of the optical fiber containing the fiber Bragg grating strain sensor arrays are embedded into a monolithic structure. By co-locating these strain sensors down the length of the structure whereby sensing points are created, the differential strain between the cores is used to calculate curvature along the length of the structure. By knowing the curvature of the structure at each individual sensing point the overall shape of the structure is reconstructed, presuming that each individual sensing point is sufficiently small.

Figure 5:
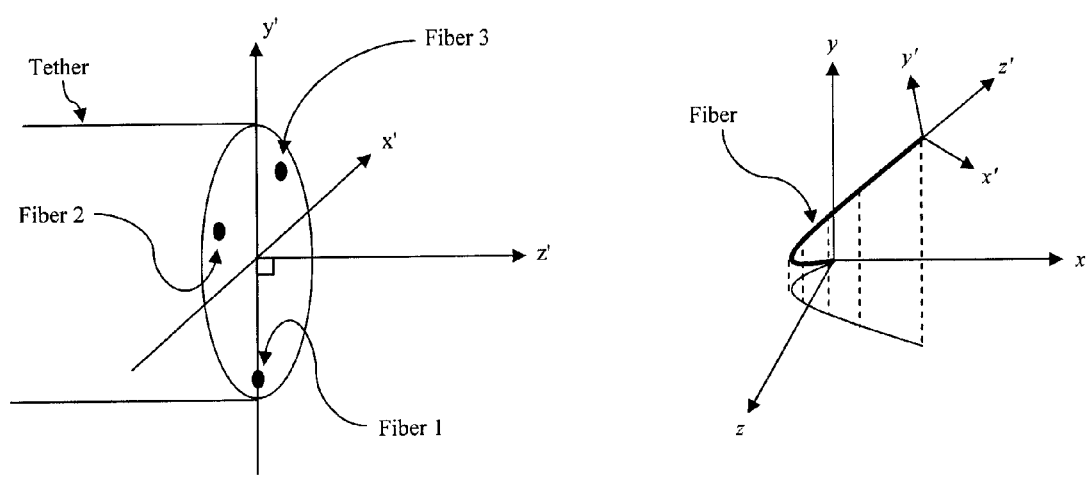
FIG. 5 depicts a sensor frame.
Figure 6:
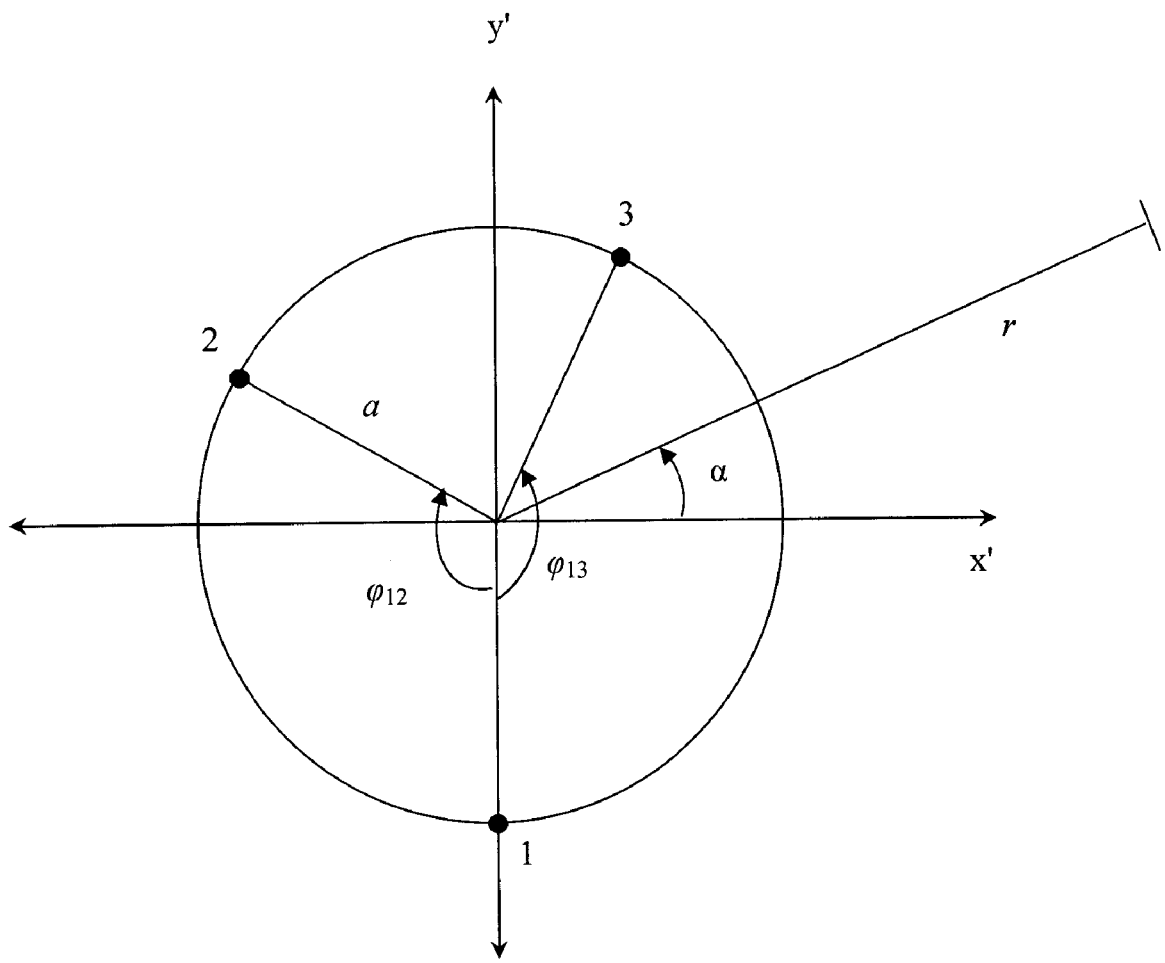
FIG. 6 is a bend parameter schematic.
Figure 7:
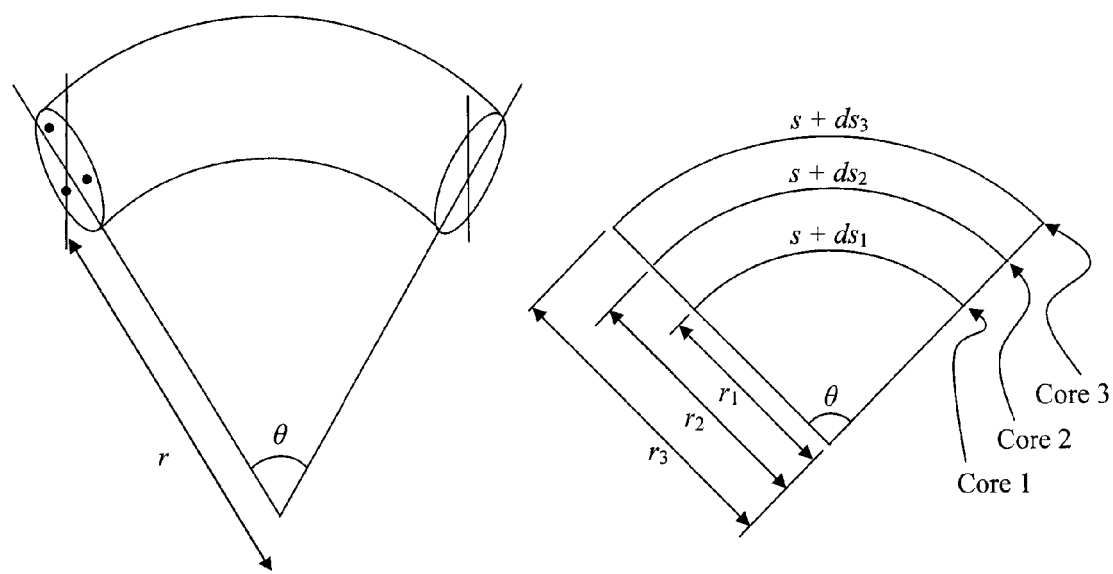
FIG. 7 depicts the bend geometry.

Strain values for each segment of an object (such as a tether) are used to compute a bend angle and bend radius for each segment of the object. Starting from the beginning of the object, this data is then used to compute the location of the next sensor triplet along the object and to define a new local coordinate system. An algorithm interpolates circular arcs between each sensor triplet on the object. The geometry of the remainder of the object is determined by repeating the process for each sensor triplet along the length of the object. Since the fiber Bragg gratings in each sensing fiber are collocated, a triplet of strain values at evenly spaced segments along the object exists. For each step along the object, a local coordinate system (x', y', z') is defined called the sensor frame. This coordinate system has its origin at the center of the object's perimeter for any given sensor triplet. The z' axis points in the direction of the object and the y' axis is aligned with fiber 1. (See FIG. 5.) Using the three strain values ($\epsilon_1$, $\epsilon_2$, $\epsilon_3$) for a given sensor triplet one can calculate the direction of the bend, $\alpha$, with respect to the x' axis as well as the bend radius, r, which is the distance from the center of curvature to the center of the core perimeter (see FIG. 6). Knowing r and $\alpha$ for a particular object segment permits the computation of the coordinates of the end of the segment in the (x', y', z') coordinate system. The beginning of the fiber segment is taken to be the origin of the (x', y', z') system. When there is no curvature to the fiber segment, each core segment has a length s. When a curvature is introduced each core is generally a different distance ($r_1$, $r_2$, $r_3$) from the center of curvature, as shown in FIG. 7. Since all of the core segments subtend the same curvature angle, $\theta$, each segment must have a different length. The change in length due to bending the fiber is denoted as $ds_1$, $ds_2$ and $ds_3$ as shown in FIG. 7.

From the geometry shown in FIG. 7, the equations relating the change in length and radius of curvature of each fiber to the other fibers are derived as:

$$\theta = \frac{s+ds_1}{r_1} = \frac{s+ds_2}{r_2} = \frac{s+ds_3}{r_3} \quad (1)$$

Since strain (denoted by $\epsilon$) is defined as the ratio of the change in length of the fiber, ds to its unstretched length s (i.e. $\epsilon=ds/s$) the first part of Equation 1 is written in terms of the measured strains.

$$\theta = \frac{s+ds_1}{r_1} = s\left(\frac{1+ds_1/s}{r_1}\right) = s\left(\frac{1+\varepsilon_1}{r_1}\right) \quad (2)$$

Extending this argument to the other terms of Equation 1 the following expression results:

$$\frac{1+\varepsilon_1}{r_1} = \frac{1+\varepsilon_2}{r_2} = \frac{1+\varepsilon_3}{r_3} \quad (3)$$

Figure 8:
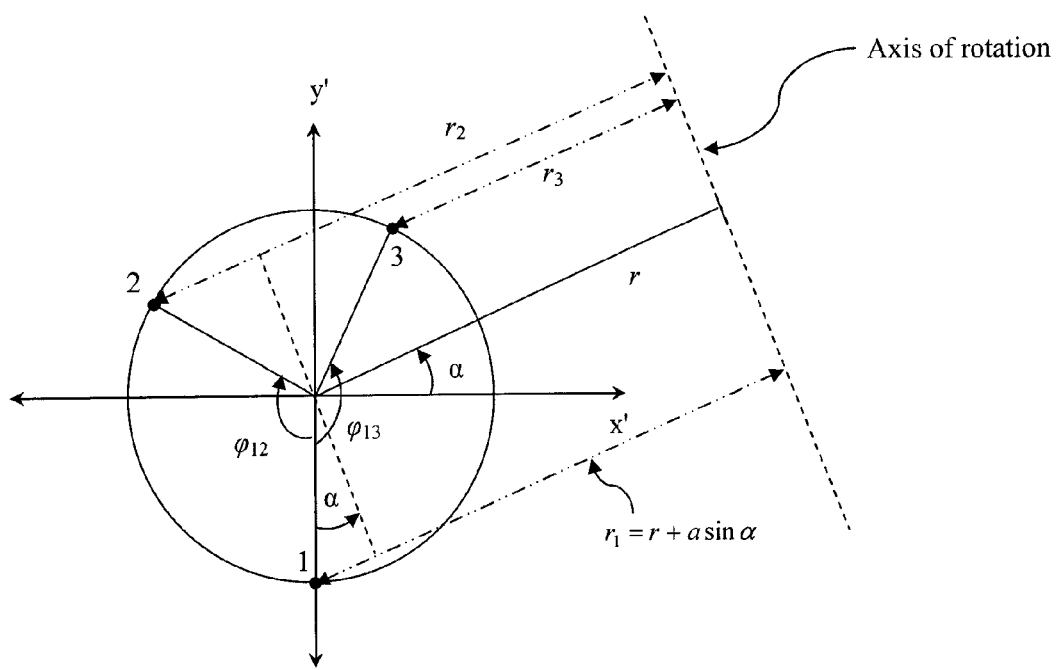

In order to solve Equation 3 for r and $\alpha$, $r_1$, $r_2$, and $r_3$ need to be written in terms of r and $\alpha$. This can be done by analyzing the geometry of the fiber cross-section (FIG. 8) and results in the following expressions for the radii of curvature for each of the fibers:

$$r_1 = r + \alpha \sin\alpha$$

$$r_2 = r + \alpha \sin(\alpha+\phi_{12})$$

$$r_2 = r + \alpha \sin(\alpha-\phi_{13}) \quad (4)$$

Using Equations 4 to make substitutions in Equations 3 the following three equations are derived for r and $\alpha$. These equations are:

$$(1+\epsilon_1)(r+\alpha \sin(\alpha+\phi_{12})) = (1+\epsilon_2)(r+\alpha \sin(\alpha))$$

$$(1+\epsilon_1)(r+\alpha \sin(\alpha-\phi_{13})) = (1+\epsilon_3)(r+\alpha \sin(\alpha))$$

$$(1+\epsilon_2)(r+\alpha \sin(\alpha-\phi_{13})) = (1+\epsilon_3)(r+\alpha \sin(\alpha+\phi_{12})) \quad (5)$$

In order to make these equations easier to follow the following substitutions are made.

$$\epsilon_{12} = \epsilon_2 - \epsilon_1 \quad \epsilon_{13} = \epsilon_3 - \epsilon_1 \quad \epsilon_{23} = \epsilon_3 - \epsilon_2$$

$$\sigma_1 = 1+\epsilon_1 \quad \sigma_2 = 1+\epsilon_2 \quad \sigma_3 = 1+\epsilon_3 \quad (6)$$

After a bit of algebra the following solution is found for $\alpha$.

$$\tan\alpha = \frac{\varepsilon_{13}\sin\varphi_{12} + \varepsilon_{12}\sin\varphi_{13}}{\varepsilon_{23} - \varepsilon_{13}\cos\varphi_{12} + \varepsilon_{12}\cos\varphi_{13}} \quad (7)$$

It is clear from Equation 7 that the bend angle is dependent only on the differential strains, not the absolute strain values. The bend radius r can be computed in three different ways.

Each of these formulae give the same solution for r but it is useful during implementation to have at least two handy in case one of the differential strains (defined in Equations 6) turns out to be zero.

$$r = \begin{cases} \dfrac{a}{\varepsilon_{12}}(\sigma_1 \sin(\alpha + \varphi_{12}) - \sigma_2 \sin(\alpha)) \\ \dfrac{a}{\varepsilon_{13}}(\sigma_1 \sin(\alpha - \varphi_{13}) - \sigma_3 \sin(\alpha)) \\ \dfrac{a}{\varepsilon_{23}}(\sigma_2 \sin(\alpha - \varphi_{13}) - \sigma_3 \sin(\alpha + \varphi_{12})) \end{cases} \quad (8)$$

Clearly, Equation 7 shows that $-\pi/2 < \alpha < \pi/2$. The extra $\pi$ radians appear in the r calculation. That is, if r is negative, simply negate r and add $\pi$ to $\alpha$. After this operation, r>0 and $0 \leq \alpha < 2\pi$. Also, when implementing an algorithm, cases where $\epsilon_1 = \epsilon_2 = \epsilon_3$ form a special case where the bend angle is arbitrary because the bend radius is infinite (zero curvature).

SENSOR FRAME POSITION CALCULATION. Knowing r and a for $\alpha$ particular tether segment permits the computation of the coordinates of the end of the segment in the (x', y', z') coordinate system. The beginning of the fiber segment is taken to be the origin of the (x', y', z') system. From FIG. 9 the relationship between (r, $\alpha$) and the endpoint of the segment (x', y', z') can be derived. The angle $\theta$, shown in the diagram is related to the bend radius, r, and the tether segment length, s, through $\theta = s/r$.

Figure 9:
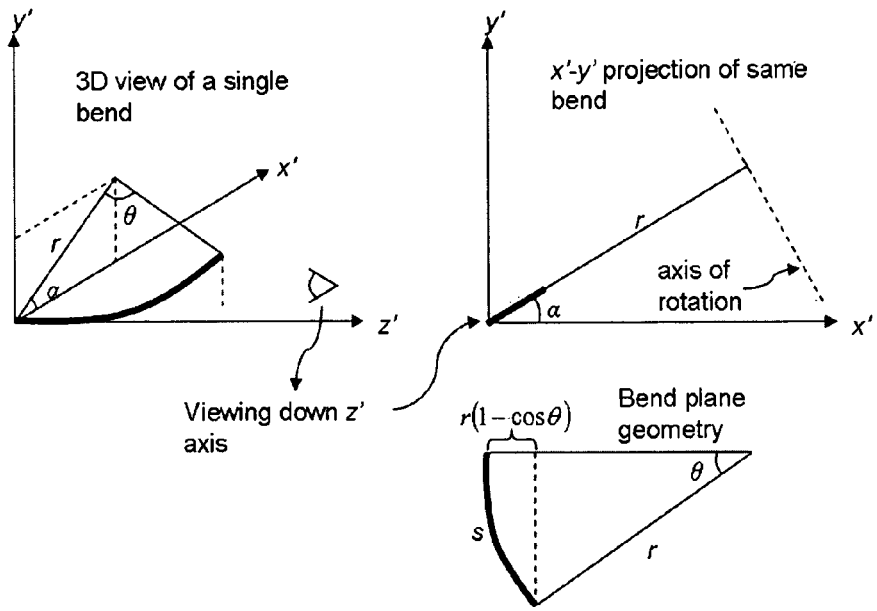
FIG. 9 illustrates bend plane geometry.

From FIG. 9 it is not difficult to see that the proper expressions for the coordinates of the end of the tether are given by $$x' = r(1 - \cos\theta)\cos\alpha$$

$$y' = r(1 - \cos\theta)\sin\alpha$$

$$z' = r\sin\theta \quad (9)$$

LABORATORY FRAME POSITION CALCULATION. In order to reference the coordinates (x', y', z') back to the laboratory frame of reference (x, y, z), the orientation of the $\hat{x}'$, $\hat{y}'$, $\hat{z}'$ basis vectors with respect to the lab frame for each segment of the tether must be tracked. In order to accomplish this, a rotation matrix is utilized that will rotate a vector through an angle $\theta$ about an axis of rotation. This rotation is performed with the rotation matrix, R, defined as follows:

$$R(\alpha, \theta) = R_{z'}(-\alpha) R_{y'}(\theta) R_{z'}(\alpha) \quad (10)$$

1. Align y's axis with axis of rotation
2. Rotate through $\theta$ about y' axis.
3. Undo step 1

$$R_{z'}(\alpha) = \begin{bmatrix} \cos\alpha & \sin\alpha & 0 \\ -\sin\alpha & \cos\alpha & 0 \\ 0 & 0 & 1 \end{bmatrix} \quad R_{y'}(\theta) = \begin{bmatrix} \cos\theta & 0 & \sin\theta \\ 0 & 1 & 0 \\ -\sin\theta & 0 & \cos\theta \end{bmatrix}. \quad (11)$$

The transformation matrix R, after multiplying the three rotation matrices is:

$$R(\alpha, \theta) = \quad (12)$$

$$\begin{bmatrix} \cos(\theta)\cos^2(\alpha) + \sin^2(\alpha) & (\cos\theta - 1)\sin(\alpha)\cos(\alpha) & \sin(\theta)\cos(\alpha) \\ (\cos(\theta) - 1)\sin(\alpha)\cos(\alpha) & \cos(\theta)\sin^2(\alpha) + \cos^2(\alpha) & \sin(\theta)\sin(\alpha) \\ -\sin(\theta)\cos(\alpha) & -\sin(\theta)\sin(\alpha) & \cos(\theta) \end{bmatrix}.$$

The rotation matrix R is used to translate the basis vectors from one segment of the tether into basis vectors for the next segment in terms of the first segment's basis vectors. The subscript 'n' signifies variables related to the $n^{th}$ tether segment. The notation $R_n^{ij}$ refers to particular elements (row i, column j) of the rotation matrix $R(\alpha_n, \theta_n)$ given in equation 12 for the $n^{th}$ sensor triplet. Also, the subscript n on the column vectors denotes that these vectors are referenced to the ($\hat{x}_n'$, $\hat{y}_n'$, $\hat{z}_n'$) basis.

$$\hat{x}'_{n+1} = R(\alpha_n, \theta_n) \begin{bmatrix} 1 \\ 0 \\ 0 \end{bmatrix}_n = \begin{bmatrix} R_n^{11} \\ R_n^{21} \\ R_n^{31} \end{bmatrix}_n = R_n^{11} \hat{x}'_n + R_n^{21} \hat{y}'_n + R_n^{31} \hat{z}'_n \quad (13)$$

$$\hat{y}'_{n+1} = R(\alpha_n, \theta_n) \begin{bmatrix} 0 \\ 1 \\ 0 \end{bmatrix}_n = \begin{bmatrix} R_n^{12} \\ R_n^{22} \\ R_n^{32} \end{bmatrix}_n = R_n^{12} \hat{x}'_n + R_n^{22} \hat{y}'_n + R_n^{32} \hat{z}'_n$$

$$\hat{z}'_{n+1} = R(\alpha_n, \theta_n) \begin{bmatrix} 0 \\ 0 \\ 1 \end{bmatrix}_n = \begin{bmatrix} R_n^{13} \\ R_n^{23} \\ R_n^{33} \end{bmatrix}_n = R_n^{13} \hat{x}'_n + R_n^{23} \hat{y}'_n + R_n^{33} \hat{z}'_n$$

Equations 13 represent a recursion relation for the orientation of any given segment of the sensing fiber. If the prime coordinate system initially coincides with the lab system:

$$\hat{x}_1' = \hat{x} \quad \hat{y}_1' = \hat{y} \quad \hat{z}_1' = \hat{z} \quad (14)$$

Starting with the basis vectors given in equations 14, equations 13 can then be used to compute the basis vectors at any point along the tether in terms of the laboratory basis vectors ($\hat{x}$, $\hat{y}$, and $\hat{z}$). That is, the sensor frame basis vectors for any sensor triplet along the tether may be written in the following form:

$$\hat{x}_n' = c_n^{11} \hat{x} + c_n^{12} \hat{y} + c_n^{13} \hat{z}$$

$$\hat{y}_n' = c_n^{21} \hat{x} + c_n^{22} \hat{y} + c_n^{23} \hat{z}$$

$$\hat{z}_n' = c_n^{31} \hat{x} + c_n^{32} \hat{y} + c_n^{33} \hat{z} \quad (15)$$

By using the general expressions of equations 15 in conjunction with the recursion relations in equations 12, a general expression for the constants $c_n^{ij}$ in equation 15 can be written. First consider the term $c_{n+1}^{11}$. It is known from equations 13 that $$\hat{x}_{n+1}' = R_n^{11} \hat{x}_n' + R_n^{21} \hat{y}_n' + R_n^{31} \hat{z}_n'. \quad (16)$$

Therefore the component of $\hat{x}_{n+1}'$ in the $\hat{x}$ direction (i.e.—$c_{n+1}^{11}$) must include any components of $\hat{x}_n'$, $\hat{y}_n'$, and $\hat{z}_n'$ and that are in the $\hat{x}$ direction. These components are shown in equations 15. Therefore the following expression for $c_{n+1}^{11}$ can be derived:

$$c_{n+1}^{11} = R_n^{11} c_n^{11} + R_n^{21} c_n^{21} + R_n^{31} c_n^{31} \quad (17)$$

Following the same procedure for $c_{n+1}^{12}$:

$$c_{n+1}^{12} = R_n^{11} c_n^{12} + R_n^{21} c_n^{22} + R_n^{31} c_n^{32}. \quad (18)$$

Now a general recursion relation for $c_{n+1}^{ij}$ can be shown to be:

$$c_{n+1}^{ij} = \sum_{k=1}^{3} R_n^{ki} c_n^{kj} \quad (19)$$

From equations 14 it can be seen that the initial conditions for this relation are given by:

$$c_1^{ij} = \begin{bmatrix} 1 & 0 & 0 \\ 0 & 1 & 0 \\ 0 & 0 & 1 \end{bmatrix}. \quad (20)$$

The necessary information to construct the relative position of the tether in the laboratory frame now exists. For the $n^{th}$ tether segment, the displacement vector, $w_n$, from start to end is given by the expression:

$$w_n = x_n' \hat{x}_n' + y_n' \hat{y}_n' + z_n' \hat{z}_n'. \quad (21)$$

The components of $w_n$ are given by equations 9, while the basis vectors can be referenced to the lab frame via equations 15 & 19. Having $w_n$ in the lab basis vectors ($\hat{x}$, $\hat{y}$, $\hat{z}$), an expression for the position, $s_n$, of the end of the $n^{th}$ segment of the tether in the lab frame is then derived to be:

$$s_n = \sum_{m=1}^{n} w_m. \quad (22)$$

The previous sections described a method for finding the location of the center point on the tether from strain data for collocated sensors. In order to implement this algorithm in software it seems that a good approach is to take advantage of the recursion relations that were developed by starting at the beginning of the tether (where the lab and sensor frames coincide) and computing the endpoint of each tether in the laboratory frame sequentially. Previously, the equations necessary to translate the strains from each sensor triplet along the tether into a list of bend radii $r_n$ and angles $\alpha_n$ as well as the position of the end of a tether segment in the sensor frame of reference were derived. Generalizing these results to the $n^{th}$ tether segment yields:

$$x_n' = r_n(1 - \cos\theta_n)\cos\alpha_n$$

$$y_n' = r_n(1 - \cos\theta_n)\sin\alpha_n,$$

$$z_n' = r_n \sin\theta_n \quad (23)$$

where $\theta_n = s/r_n$. In addition, the relationship between the sensor frame coordinates and the laboratory frame coordinates was derived. Using these relationships, a recursive relationship for the position of the end of any tether segment in the laboratory frame can be derived as follows:

$$s_n = \sum_{m=1}^{n} w_m = \sum_{m=1}^{n} x_m' \hat{x}_m' + y_m' \hat{y}_m' + z_m' \hat{z}_m', \quad (24)$$

where the basis vectors are referenced to the laboratory reference frame by:

$$\hat{x}_n' = c_n^{11} \hat{x} + c_n^{12} \hat{y} + c_n^{13} \hat{z} \quad (25)$$

$$\hat{y}_n' = c_n^{21} \hat{x} + c_n^{22} \hat{y} + c_n^{23} \hat{z},$$
$$\hat{z}_n' = c_n^{31} \hat{x} + c_n^{32} \hat{y} + c_n^{33} \hat{z}$$

and $$c_{n+1}^{ij} = \sum_{k=1}^{3} R_n^{ki} c_n^{kj}, \quad (26)$$

where $R_n^{ij}$ is given by:

$$R_n^{ij} = \begin{bmatrix} \cos(\theta_n)\cos^2(\alpha_n) + \sin^2(\alpha_n) & (\cos\theta_n - 1)\sin(\alpha_n)\cos(\alpha_n) & \sin(\theta_n)\cos(\alpha_n) \\ (\cos(\theta_n) - 1)\sin(\alpha_n)\cos(\alpha_n) & \cos(\theta_n)\sin^2(\alpha_n) + \cos^2(\alpha_n) & \sin(\theta_n)\sin(\alpha_n) \\ -\sin(\theta_n)\cos(\alpha_n) & -\sin(\theta_n)\sin(\alpha_n) & \cos(\theta_n) \end{bmatrix}, \quad (27)$$

with the initial condition $$c_1^{ij} = \begin{bmatrix} 1 & 0 & 0 \\ 0 & 1 & 1 \\ 0 & 0 & 1 \end{bmatrix}. \quad (28)$$

Therefore, equations 23-28 in conjunction with the solutions for $\alpha$ and $r$ given in equations 7 and 8 form the set of results necessary to translate measured strain data into three dimensional position data.

EXAMPLES

Example 1

Shape sensors wherein the optical fiber means comprises three single core optical fibers were surface attached to the outside of an inflatable isogrid boom that was approximately 1.2 m in length. The fiber optic sensor arrays, each containing approximately 120 sensors with a 0.5 cm gauge length spaced at 1 cm intervals, center-to-center, ran along the entire axial length of the boom oriented 120° with respect to each other. The boom was fixed at one end while the other end was unattached in a classic cantilever beam set-up. Various weights were then placed on the free-floating end while strain measurements were taken to monitor the dynamic shape of the structure. A standard height gauge was used to directly measure the deflection of the end of the boom for the purposes of data correlation. Upon comparison of the data, there was an excellent correlation between the fiber optic shape sensors and the height gauge. With a mass of 2.5 kg suspended from the end, the height gauge indicated a deflection of 1.7 mm while the fiber optic shape sensors indicated a deflection of 1.76 mm with a mass of 4 kg suspended from the end, the height gauge indicated a deflection of 2.7 mm while the fiber optic shape sensors indicated a deflection of 2.76 mm.

Example 2

Figure 10:
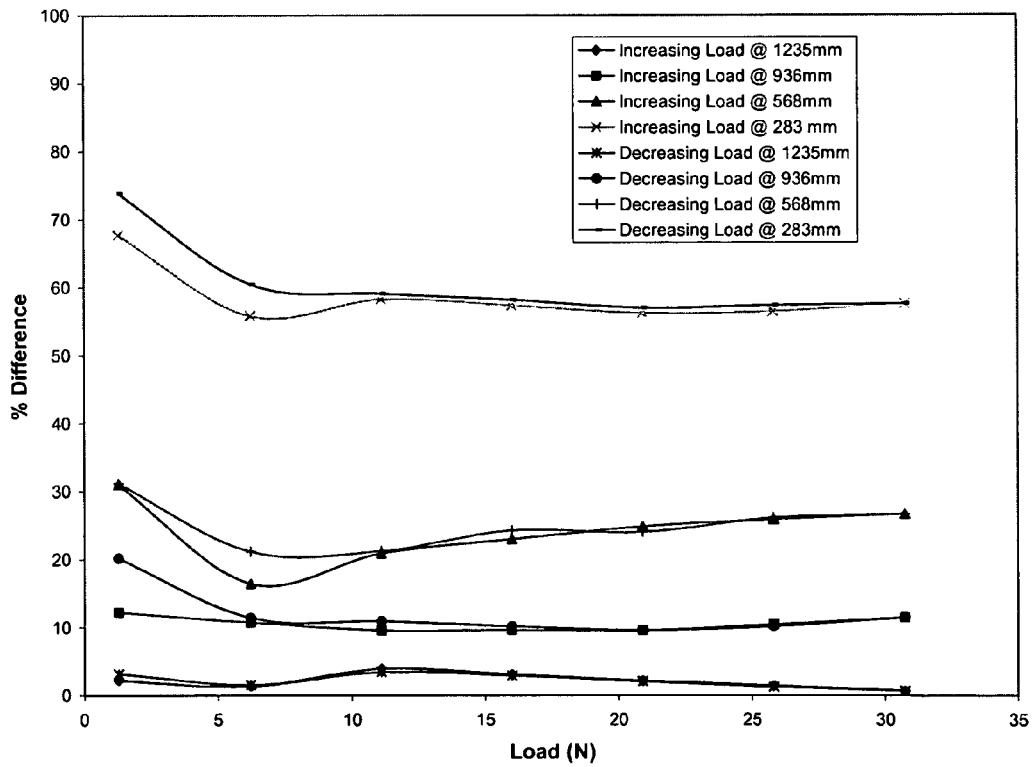
FIG. 10 is a graphical representation of the percent error between the laser displacement sensors and the fiber optic shape sensors.

An isogrid boom was fixed at one end while the other end was unattached in a classic cantilever beam set-up. Various weights were then placed on the free-floating end while measurements were taken to monitor the shape/relative position of the structure using the fiber optic position and shape sensing device of the present invention. Laser displacement sensors at four locations were suspended above the boom to directly measure the deflection of the boom for the purposes of data correlation. Table 1 shows the percent error between the laser displacement sensors and fiber optic shape sensors. This data is depicted graphically in FIG. 10.

TABLE 1

| | Sensor Location (mm) | | | |
|---|---|---|---|---|
| Load (g) | 1235 | 936 | 568 | 283 |
| 0 | | | | |
| 132 | 2.19 | 12.2 | 31.0 | 67.7 |
| 623 | 1.34 | 10.8 | 16.5 | 55.8 |
| 1132 | 3.91 | 9.56 | 21.0 | 58.3 |
| 1632 | 3.09 | 9.64 | 23.0 | 57.4 |
| 2132 | 2.13 | 9.55 | 24.8 | 56.2 |
| 2632 | 1.40 | 10.5 | 25.9 | 56.5 |
| 2132 | 2.05 | 9.58 | 24.0 | 57.0 |
| 1632 | 2.90 | 10.2 | 24.3 | 58.2 |
| 1132 | 3.45 | 10.9 | 21.3 | 59.2 |
| 632 | 1.56 | 11.4 | 21.2 | 60.5 |
| 132 | 3.19 | 20.2 | 31.2 | 73.9 |
| 0 | | | | |
| Average | 2.24 | 11.2 | 24.4 | 59.7 |

At each load, anywhere from 127 to 192 measurements were taken using the Luna Distributed Sensing System unit commercially available from Luna Innovations Incorporated. The standard deviations of the shape data for each load at the same four points along the tether showed that in the worst case, the standard deviation is 14 µm, indication a very high degree of reproducibility.

Example 3

An oscillator (LDS v-203 electrodynamic shaker) driven by a function generator and amplified by a power amplifier was attached to the free end of an isogrid boom which was attached in a classic cantilever beam configuration. A sinusoidal signal was used to drive the shaker with a displacement amplitude of roughly 1.6 mm, peak-to-peak (0.566 RMS) and frequencies of 0.5 and 1.0 Hz. The fiber optic position and shape sensing device of the present invention was attached to the isogrid boom and was used to capture dynamic shape data at roughly 2.189 Hz. Using the dynamic shape data captured by the sensing device while the beam was oscillating, modal analysis was performed. Approximately 2853 samples were taken at the 0.5 Hz oscillation mode. The frequency of oscillation was pinpointed to within roughly ±0.0004 Hz. The 1.0 Hz oscillation mode was sampled 240 times, yielding an accuracy of approximately ±0.0046 Hz. The results of this test show that the fiber optic position and shape sensing device is useful to characterize the dynamic performance of a mechanical structure.

Example 4

A series of shape measurements of a 3 m long vertically suspended isogrid boom were performed. The fiber optic position and shape sensing device of the present invention, containing approximately 300 fiber Bragg grating sensors in each of 3 cores with a 0.5 cm gauge length spaced at 1 cm intervals, center-to-center, were positioned along the outside surface of the boom along the entire axial length oriented 120° with respect to each other. The measurements included cantilever bending, axial loading, and dynamic bending (approximately 5 Hz). Comparisons were made with a deflection gauge and were found to correlate to within ±0.5 mm over the full length of the isogrid boom.

The above description and drawings are only illustrative of preferred embodiments which achieve the objects, features and advantages of the present invention, and it is not intended that the present invention be limited thereto. Any modification of the present invention which comes within the spirit and scope of the following claims is considered part of the present invention.

What is claimed is:

1. A fiber optic position and shape sensing device comprising:
   an optical fiber including at least two fiber cores spaced apart so that mode coupling between the fiber cores is minimized;
   an array of fiber Bragg gratings disposed within each fiber core;
   a frequency domain reflectometer positioned in an operable relationship to the optical fiber for determining a measured strain parameter at a number points along each core in the optical fiber; and
   a computing device for determining:
      a differential strain parameter between the cores at each location along the fiber,
      one or more local bend parameters along the length of the fiber based on the determined differential strain parameter value at each of the number points along the optical fiber, and
      a shape of the object based on the one or more local bend parameters,
   wherein the number of points is sufficiently large to permit determination of the shape of the object with an accuracy better than one percent of a length of the optical fiber.

2. A fiber optic position and shape sensing device according to claim 1, wherein the optical fiber includes at least two single core optical fibers.

3. A fiber optic position and shape sensing device according to claim 2, wherein the optical fiber includes three cores, wherein the three cores are non-coplanar and form a triangular shape, and wherein the computing device is configured to determine differential strain parameter values between the three cores and to calculate a bend angle and a bend radius based on differential strains determined between the three cores.

4. A fiber optic position and shape sensing device according to claim 3, wherein the three fiber cores each have a center, wherein each center is 120° with respect to each of the other two core centers.

5. A fiber optic position and shape sensing device according to claim 2, wherein the array of fiber Bragg gratings are collocated along each single core optical fiber.

6. A fiber optic position and shape sensing device according to claim 1, wherein the array of fiber Bragg gratings comprises at least one hundred fiber Bragg gratings.

7. A fiber optic position and shape sensing device according to claim 1, wherein the optical fiber means is a multicore optical fiber.

8. A fiber optic position and shape sensing device according to claim 7, wherein the multicore optical fiber comprises three fiber cores.

9. A fiber optic position and shape sensing device according to claim 8, wherein the three fiber cores are non-coplanar and form a triangular shape.

10. A fiber optic position and shape sensing device according to claim 9, wherein the three fiber cores each have a center, wherein each center is 120° with respect to each of the other two core centers.

11. A fiber optic position and shape sensing device according to claim 7, wherein the array of fiber Bragg gratings are co-located along the multicore optical fiber.

12. A fiber optic position and shape sensing device according to claim 11, wherein the array of fiber Bragg gratings is comprised of at least one hundred fiber Bragg gratings.

13. A fiber optic position and shape sensing device according to claim 1, further comprising a broadband reference reflector positioned in an operable relationship to each fiber Bragg grating array wherein the frequency domain reflectometer receives signals from each fiber Bragg grating array establishing an optical path length for each reflector/grating relationship.

14. A fiber optic position and shape sensing device according to claim 1, wherein the fiber optic position and shape sensing device is a medical instrument.

15. A fiber optic position and shape sensing device according to claim 14, wherein the medical instrument is an instrument used for surgery.

16. A fiber optic position and shape sensing device according to claim 14, wherein the medical instrument is an instrument used for biometric monitoring.

17. The apparatus in claim 1, wherein the number of points is sufficiently large to permit accurate determination of a shape of the object with an accuracy better than 0.1 percent of a length of the optical fiber.

18. The apparatus in claim 1, wherein the array of fiber Bragg gratings disposed within each fiber core includes gratings with overlapping spectra closer than 10 cm together.

19. The apparatus in claim 1, wherein the array of fiber Bragg gratings disposed within each fiber core includes gratings that have less than 1 percent reflectivity.

20. The apparatus in claim 1, wherein the array of fiber Bragg gratings disposed within each fiber core includes gratings that have less than 0.1 percent reflectivity.

21. A fiber optic method for determining the position and shape of an object, the method comprising the steps of:
a) providing an object;
b) providing a fiber optic position and shape sensing device comprising:
a multi-core optical fiber for determining position and shape of the object, the multi-core optical fiber comprising at least two fiber cores spaced apart wherein mode coupling between the fiber cores is minimized, where an array of fiber Bragg gratings is disposed within each fiber core, and
a frequency domain reflectometer positioned in an operable relationship to the multi-core optical fiber;
c) affixing the multi-core optical fiber to the object;
d) measuring with the frequency domain reflectometer strain at a number of points on each core in the optical fiber;
e) determining a differential strain parameter between the cores at each point along the fiber;
f) calculating one or more local bend parameters along the fiber based on the determined differential strain parameters; and
g) determining a shape of the object based on the calculated one or more local bend parameters,
where the number of points is sufficiently large to permit determination of the shape of the object with an accuracy better than one percent of a length of the optical fiber.

22. A fiber optic method according to claim 21, wherein the array of fiber Bragg gratings is comprised of at least one hundred fiber Bragg gratings.

23. A fiber optic method according to claim 21, wherein the object is a position tracking device.

24. A fiber optic method according to claim 23, wherein the position tracking device is a robot.

25. A fiber optic method according to claim 21, wherein the optical fiber means comprises three cores and wherein the object has a three dimensional shape.

26. A fiber optic method according to claim 21, wherein the object is a flexible object.

27. A fiber optic method according to claim 26, wherein the flexible object is a medical instrument or a flexible structure.

28. A fiber optic method according to claim 21, wherein the number of points is sufficiently large to permit accurate determination of a shape of the object with an accuracy better than 0.1 percent of a length of the optical fiber.

29. A fiber optic method according to claim 21, wherein the array of fiber Bragg gratings disposed within each fiber core includes gratings with overlapping spectra closer than 10 cm together.

30. A fiber optic method according to claim 21, wherein the array of fiber Bragg gratings disposed within each fiber core includes gratings that have less than 1 percent reflectivity.

31. A fiber optic method according to claim 21, wherein the array of fiber Bragg gratings disposed within each fiber core includes gratings that have less than 0.1 percent reflectivity.

32. A fiber optic method according to claim 21, wherein the array of fiber Bragg gratings disposed within each fiber core includes gratings that have less than 0.1 percent reflectivity.

33. A medical instrument system, comprising:
an elongate instrument body;
an optical fiber at least partially encapsulated in a wall of the elongate instrument body, the optical fiber including three fiber cores having one or more Bragg gratings;
a detector corresponding to a frequency domain reflectometer operatively coupled to a proximal end of the optical fiber and configured to detect respective light signals reflected by the one or more Bragg gratings at a number points along each core in the optical fiber; and
a controller operatively coupled to the detector and configured to determine a geometric configuration of at least a portion of the elongate instrument body based on an analysis of the detected reflected portions of the light signals from which differential strain values between the cores at each point along the fiber are determined,
where the number of points is sufficiently large to permit accurate determination of the geometric configuration of at least a portion of the elongate instrument body with an accuracy better than one percent of a length of the optical fiber.

34. The medical instrument system of claim 33, wherein the elongate instrument body is flexible.

35. The medical instrument system of claim 33, wherein the elongate instrument body is robotically controlled.

36. The medical instrument system of claim 33, wherein the elongate instrument body is manually controlled.

37. The medical instrument system of claim 33, further comprising a reference reflector coupled to the optical fiber in an operable relationship with the one or more Bragg gratings.

38. The medical instrument system of claim 33, wherein the optical fiber comprises a plurality of fiber cores, each core having one or more Bragg gratings.

39. The medical instrument system of claim 33, the fiber core comprising a plurality of spaced apart Bragg gratings.

40. The medical instrument system of claim 33, wherein the optical fiber is substantially encapsulated in a wall of the elongate instrument body.

41. The medical instrument system of claim 33, wherein the elongate instrument body defines an interior lumen, and wherein the optical fiber is partially disposed in the lumen.

42. The medical instrument system of claim 33, the elongate instrument body having a wall, the wall defining an embedded lumen, wherein the optical fiber is disposed in the embedded lumen.

43. The medical instrument system of claim 33, the elongate instrument body having a neutral axis of bending, the optical fiber being coupled to the elongate instrument body so as to be substantially aligned with the neutral axis of bending when the elongate instrument body is in a substantially unbent configuration, and to move relative to the neutral axis of bending as the elongate instrument body undergoes bending.

44. The medical instrument system of claim 33, the elongate instrument body having a neutral axis of bending, the optical fiber being coupled to the elongate instrument body so as to be substantially aligned with the neutral axis of bending regardless of bending of the elongate instrument body.

45. The medical instrument system of claim 33, the elongate instrument body having a neutral axis of bending, the optical fiber being coupled to the elongate instrument body so as to remain substantially parallel to, but not coaxial with, the neutral axis of bending, regardless of bending of the elongate instrument body.

46. The medical instrument system of claim 33, wherein the elongate instrument body is a catheter body.

47. The medical instrument system of claim 33, wherein the analysis is a spectral analysis.

* * * * *